US009338207B2

(12) United States Patent
Lingley

(10) Patent No.: US 9,338,207 B2
(45) Date of Patent: *May 10, 2016

(54) REMOTE CINE VIEWING OF MEDICAL IMAGES ON A ZERO-CLIENT APPLICATION

(71) Applicant: Merge Healthcare Incorporated, Chicago, IL (US)

(72) Inventor: William A. N. Lingley, Liverpool (CA)

(73) Assignee: Merge Healthcare Incorporated, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/333,280

(22) Filed: Jul. 16, 2014

(65) Prior Publication Data
US 2014/0330931 A1  Nov. 6, 2014

Related U.S. Application Data

(63) Continuation of application No. 13/305,442, filed on Nov. 28, 2011, now Pat. No. 8,799,358.

(51) Int. Cl.
*H04L 29/06* (2006.01)
*H04L 29/08* (2006.01)
*G06F 3/14* (2006.01)

(52) U.S. Cl.
CPC ............... *H04L 65/60* (2013.01); *H04L 67/12* (2013.01); *G06F 3/14* (2013.01); *G09G 2350/00* (2013.01); *G09G 2370/022* (2013.01); *G09G 2370/027* (2013.01)

(58) Field of Classification Search
USPC .......................... 709/217, 229, 203, 204, 205
See application file for complete search history.

(56) References Cited

U.S. PATENT DOCUMENTS 5,085,224 A  2/1992  Galen et al.
5,211,169 A  5/1993  Freeland
5,432,871 A  7/1995  Novik
5,708,826 A  1/1998  Ikeda et al.
5,715,823 A  2/1998  Wood et al.
5,819,288 A  10/1998  DeBonet
5,891,035 A  4/1999  Wood et al.

(Continued)

FOREIGN PATENT DOCUMENTS

EP  1480154  11/2004
JP  11250160  9/1999

(Continued)

OTHER PUBLICATIONS

Agarwal, "What's the skinny on thick, thin and zero client technology for diagnostic imaging?," DOTmed Business News, May 9, 2011, Retrieved from Internet on May 20, 2011 <URL: http://www.dotmed.com/legal/print/story.html?nid=15909>.

(Continued)

*Primary Examiner* — Jude Jean Gilles
(74) *Attorney, Agent, or Firm* — Michael Best & Friedrich LLP

(57) ABSTRACT

Systems and methods for remotely viewing medical images on a client device having a zero-client web application with a buffering module. The zero-client web application receives an image series selection from a user and receives corresponding series details from a web server. The zero-client web application generates an off-screen image array according to the series details. The buffering module outputs image requests based on the series details to a web server. The web server is in communication with a medical image database storing images in a non-web browser compatible format (e.g., DICOM). The buffering module then populates the off-screen image array with converted medical images received from the web server. The zero-client web application further includes an on-screen image and a display module. The display module sequentially sets converted medical images of the off-screen array as the on-screen image to stream the converted medical images.

20 Claims, 12 Drawing Sheets

(56) References Cited

U.S. PATENT DOCUMENTS

| | | | |
|---|---|---|---|
| 5,895,461 A | 4/1999 | De-La-Huerga et al. | |
| 5,900,732 A | 5/1999 | Felmlee et al. | |
| 5,938,607 A | 8/1999 | Jago et al. | |
| 5,960,403 A | 9/1999 | Brown | |
| 5,986,662 A | 11/1999 | Argiro et al. | |
| 5,987,459 A | 11/1999 | Swanson et al. | |
| 6,006,231 A | 12/1999 | Popa | |
| 6,032,120 A | 2/2000 | Rock et al. | |
| 6,076,166 A | 6/2000 | Moshfeghi et al. | |
| 6,101,407 A | 8/2000 | Groezinger | |
| 6,243,095 B1 | 6/2001 | Shile et al. | |
| 6,256,613 B1 | 7/2001 | Falchuk et al. | |
| 6,260,021 B1 | 7/2001 | Wong et al. | |
| 6,308,171 B1 | 10/2001 | De La Huerga | |
| 6,314,452 B1 | 11/2001 | Dekel et al. | |
| 6,330,572 B1 | 12/2001 | Sitka | |
| 6,349,330 B1 | 2/2002 | Bernadett et al. | |
| 6,354,997 B1 | 3/2002 | Holley et al. | |
| 6,421,469 B1 | 7/2002 | Nelson et al. | |
| 6,424,996 B1 | 7/2002 | Killcommons et al. | |
| 6,434,569 B1 | 8/2002 | Toshimitsu et al. | |
| 6,449,639 B1 | 9/2002 | Blumberg | |
| 6,516,324 B1 | 2/2003 | Jones et al. | |
| 6,518,952 B1 | 2/2003 | Leiper | |
| 6,544,177 B1 | 4/2003 | Robinson | |
| 6,558,325 B1 | 5/2003 | Pang et al. | |
| 6,564,256 B1 | 5/2003 | Tanaka | |
| 6,581,069 B1 | 6/2003 | Robinson | |
| 6,591,272 B1* | 7/2003 | Williams | |
| 6,678,764 B2 | 1/2004 | Parvulescu et al. | |
| 6,691,153 B1 | 2/2004 | Hanson et al. | |
| 6,708,184 B2 | 3/2004 | Smith et al. | |
| 6,734,880 B2 | 5/2004 | Chang et al. | |
| 6,738,798 B1 | 5/2004 | Ploetz et al. | |
| 6,741,977 B1 | 5/2004 | Nagaya et al. | |
| 6,748,347 B1 | 6/2004 | Dalton | |
| 6,792,575 B1 | 9/2004 | Samaniego et al. | |
| 6,829,378 B2 | 12/2004 | DiFilippo et al. | |
| 6,877,134 B1 | 4/2005 | Fuller et al. | |
| 6,891,973 B1 | 5/2005 | Atsumi et al. | |
| 6,909,792 B1 | 6/2005 | Carrott et al. | |
| 6,911,916 B1 | 6/2005 | Wang et al. | |
| 6,934,698 B2 | 8/2005 | Judd et al. | |
| 7,031,504 B1 | 4/2006 | Argiro et al. | |
| 7,106,479 B2 | 9/2006 | Roy et al. | |
| 7,180,624 B2 | 2/2007 | Tipimeni | |
| 7,181,617 B2 | 2/2007 | Wise et al. | |
| 7,197,531 B2 | 3/2007 | Anderson | |
| 7,206,804 B1 | 4/2007 | Deshpande et al. | |
| 7,218,763 B2 | 5/2007 | Belykh et al. | |
| 7,257,832 B2 | 8/2007 | Beane et al. | |
| 7,330,875 B1 | 2/2008 | Parasnis et al. | |
| 7,355,608 B1 | 4/2008 | Beach | |
| 7,386,462 B2 | 6/2008 | Silva-Craig et al. | |
| 7,457,656 B2 | 11/2008 | Judd et al. | |
| 7,492,970 B2 | 2/2009 | Saito et al. | |
| 7,505,614 B1 | 3/2009 | De La Torre Bueno | |
| 7,583,861 B2 | 9/2009 | Hanna et al. | |
| 7,587,073 B2 | 9/2009 | Park | |
| 7,606,861 B2 | 10/2009 | Killcommons et al. | |
| 7,620,892 B2 | 11/2009 | Rainero et al. | |
| 7,668,835 B2 | 2/2010 | Judd et al. | |
| 7,729,928 B2 | 6/2010 | Backhaus et al. | |
| 7,786,990 B2 | 8/2010 | Wegenkittl et al. | |
| 7,787,679 B2 | 8/2010 | Wegenkittl et al. | |
| 7,809,816 B2 | 10/2010 | Johnson et al. | |
| 7,818,041 B2 | 10/2010 | Kim et al. | |
| 7,844,705 B2 | 11/2010 | Jones et al. | |
| 7,853,621 B2 | 12/2010 | Guo | |
| 7,925,521 B2 | 4/2011 | Backhaus et al. | |
| 7,958,100 B2 | 6/2011 | Judd et al. | |
| 7,961,935 B2 | 6/2011 | Howerton, Jr. | |
| 7,999,852 B2 | 8/2011 | Deroo et al. | |
| 8,073,712 B2 | 12/2011 | Jacobus et al. | |
| 8,145,503 B2 | 3/2012 | Backhaus et al. | |
| 8,166,381 B2* | 4/2012 | Judd | G06F 17/30244 715/200 |
| 8,799,358 B2* | 8/2014 | Lingley | 709/203 |
| 2002/0075496 A1 | 6/2002 | Zhang et al. | |
| 2002/0091659 A1 | 7/2002 | Beaulieu et al. | |
| 2002/0156650 A1 | 10/2002 | Klein et al. | |
| 2003/0005464 A1 | 1/2003 | Gropper et al. | |
| 2003/0013951 A1 | 1/2003 | Stefanescu et al. | |
| 2003/0140044 A1 | 7/2003 | Mok et al. | |
| 2003/0233339 A1* | 12/2003 | Downs | 707/1 |
| 2004/0103169 A1 | 5/2004 | Nolte | |
| 2004/0117439 A1 | 6/2004 | Levett et al. | |
| 2004/0148375 A1 | 7/2004 | Levett et al. | |
| 2004/0225633 A1* | 11/2004 | Jau | 707/1 |
| 2005/0187787 A1 | 8/2005 | Tomlinson et al. | |
| 2005/0197858 A1 | 9/2005 | Lindsey | |
| 2005/0197860 A1 | 9/2005 | Joffe et al. | |
| 2005/0251012 A1* | 11/2005 | Judd | G06F 17/30244 600/407 |
| 2006/0056680 A1 | 3/2006 | Stutsman | |
| 2006/0177114 A1 | 8/2006 | Tongdee et al. | |
| 2006/0242148 A1 | 10/2006 | Rothpearl et al. | |
| 2006/0242159 A1 | 10/2006 | Bishop et al. | |
| 2007/0047794 A1 | 3/2007 | Lang et al. | |
| 2007/0067252 A1 | 3/2007 | Hengerer et al. | |
| 2007/0083615 A1 | 4/2007 | Hollebeek et al. | |
| 2007/0083660 A1 | 4/2007 | Thornton | |
| 2007/0106750 A1 | 5/2007 | Moore | |
| 2007/0118550 A1 | 5/2007 | Yang et al. | |
| 2007/0124410 A1 | 5/2007 | Hofstetter | |
| 2007/0143308 A1 | 6/2007 | Takayama et al. | |
| 2007/0203748 A1 | 8/2007 | Rothpearl et al. | |
| 2007/0214235 A1 | 9/2007 | Woods et al. | |
| 2007/0223793 A1 | 9/2007 | Gutman | |
| 2008/0005059 A1 | 1/2008 | Colang et al. | |
| 2008/0021740 A1 | 1/2008 | Beane et al. | |
| 2008/0086335 A1 | 4/2008 | Matsue et al. | |
| 2008/0109250 A1 | 5/2008 | Walker et al. | |
| 2008/0140722 A1 | 6/2008 | Jakobovits | |
| 2008/0144896 A1 | 6/2008 | Burke | |
| 2008/0181472 A1 | 7/2008 | Doi et al. | |
| 2008/0250458 A1 | 10/2008 | Roman | |
| 2009/0059082 A1 | 3/2009 | Jakobovits | |
| 2009/0063552 A1 | 3/2009 | Jones | |
| 2009/0077197 A1 | 3/2009 | Eichenseer | |
| 2009/0100096 A1 | 4/2009 | Erlichson et al. | |
| 2009/0103789 A1 | 4/2009 | Danner et al. | |
| 2009/0132285 A1 | 5/2009 | Jakobovits | |
| 2009/0210809 A1 | 8/2009 | Bacus et al. | |
| 2010/0011087 A1 | 1/2010 | Hofstetter | |
| 2010/0088113 A1 | 4/2010 | Kubota | |
| 2010/0094658 A1 | 4/2010 | Mok et al. | |
| 2010/0131591 A1 | 5/2010 | Thomas et al. | |
| 2010/0146044 A1 | 6/2010 | Holmes et al. | |
| 2010/0223566 A1 | 9/2010 | Holmes et al. | |
| 2010/0246981 A1 | 9/2010 | Hu et al. | |
| 2010/0250695 A1 | 9/2010 | Shenfield et al. | |
| 2011/0110568 A1 | 5/2011 | Vesper et al. | |
| 2011/0302414 A1 | 12/2011 | Logan et al. | |
| 2011/0307571 A1 | 12/2011 | Bakke | |
| 2013/0013664 A1 | 1/2013 | Baird et al. | |

FOREIGN PATENT DOCUMENTS

| | | |
|---|---|---|
| JP | 11284682 | 10/1999 |
| JP | 2000194836 | 7/2000 |
| JP | 2003296451 | 10/2003 |
| JP | 2005131241 | 5/2005 |
| WO | 0045301 | 8/2000 |
| WO | 0106348 | 1/2001 |
| WO | 2004102412 | 11/2004 |

OTHER PUBLICATIONS

Ajax (programming) entry, Wikipedia, Aug. 11, 2011.

Ando, Y., et al, "Inter-hospital PACS designed for Tele-radiology and Tele-conference Using a Secured High Speed Network," Proc. SPIE 3662, Medical Imaging 1999: PACS Design and Evaluation: Engineering and Clinical Issues, 420-429 (Jul. 18, 1999).

(56) References Cited

OTHER PUBLICATIONS

Arenson, RL, et al, "Computers in Imaging and Health Care: Now and in the Future," J. Digital Imaging, 13(4) 145-156 (Nov. 2000).
Bai, J, et al, "Design and Development of an Interactive Medical Teleconsultation System over the World Wide Web," IEEE Trans. Infor. Technol. Biomed., 2(2), 74-79 (Jun. 1998).
Brannon, K, "Entrepreneurs with X-ray Vision," New Orleans CityBusiness, 20(30), 1 (Mar. 20, 2000).
Brown, N, et al, "Short Strategic Study: Strategy for production and maintenance of standards for interoperability within and between service departments and other healthcare domains. Interim report v2," CEN/TC 251/N00-14, CEN/TC 251 Health Informatics, Brussels, Belgium (Feb. 21, 2000).
Browning, GC, et al, "World Wide Web Interface to Digital Imaging and Communication in Medicine-Capable Image Servers," J. Digital Imaging, 9(4), 178-184 (Nov. 1996).
Camtronics Medical Systems, "Camtronics VERICS Provides Cardiology image for Westchester Medical," <http://www.embeddedstar.com/press/content/2003/5/embedded8662.html> dated May 13, 2003.
Camtronics Medical Systems, "VERICS Cardiovascular Diagnostics Department, LGHA" available as early as Mar. 30, 2010.
Camtronics Medical Systems, "VERICS PhysioLog," Bio-Medicine, available at least as early as Apr. 20, 2008.
Camtronics Medical Systems, Information (web capture Aug. 17, 2000).
Camtronics Medical Systems, News Releases (web capture Aug. 8, 2002).
Carestream Printers, Carestream Health, Aug. 2007.
Chew, SJ, et al, OphthWeb—cost-effective telemedicine for ophthalmology, HKMJ, 4(4), 300-304 (Sep. 1998).
Clunie, D., Google Groups—DICOM, May 10, 1998.
Cox, R.D., et al, "DICOM-Compliant PACS with CD-Based Image Archival," SPIE Conference on PACS Design and Evaluation: Engineering and Clinical Issues, vol. 3339, 135-142 (Feb. 1998).
DeJarnete, WT, "Web technology and its relevance to PACS and teleradiology," Appl. Radiol., 29(8) (Aug. 2000).
Emageon Inc, "ADAC HealthCare Information Systems Uses Imageon Solutions' DICOM Products," Apr. 20, 2000 (web capture Aug. 16, 2000).
Emageon Inc, "e-CIMS Online User's Guide," V1.0, Mar. 30, 2000.
Emageon Inc, "Enterprise Web Distribution" (web capture Aug. 16, 2000).
Emageon Inc, "Imageon Solutions Changes its Name to Emageon," May 31, 2000 (web capture Aug. 16, 2000).
Emageon Inc, "Imageon Solutions teams with BellSouth to Provide Web-Enabled Enterprise Archiving of Diagnostic images to Healthcare Industry," May 24, 2000 (web capture Aug. 16, 2000).
Emageon Inc, "Web-enabled Enterprise Archive and Distribution Solution for Diagnostic Images," Aug. 15, 2000.
Feingold, E, et al, "Web Based Radiology Applications for Clinicians and Radiologists," Proc. SPIE, 3035, 60-71 (1997).
Foos, DH, et al, "Dynamic Viewing Protocols for Diagnostic Image Comparison," SPIE, Medical Imaging 1999: Image Perception and Performance, vol. 3663, 108-120 (Feb. 1999).
Foos, DH, et al, "JPEG 2000 Compression of Medical Imagery," SPIE, PACS Design and Evaluation: Engineering and Clinical Issues, vol. 3980, 85-96 (Feb. 2000).
Gidron, Y, et al, "Phased Development of a Web-Based PACS Viewer," SPIE, PACS Design and Evaluation: Engineering and Clinical Issues, vol. 3980, 486-494 (Feb. 2000).
Gilespy, T. "Optimized Algorithms for Displaying 16-bit Gray Scale Images on 8-bit Computer Graphic Systems," J. Digit. Imag., 6(1), 25-29 (Feb. 1993).
Gilespy, T. et al, "Dual Lookup Table Algorithm: An Enhanced Method of Displaying 16-Bit Gray-Scale Images on 8-Bit RBG Graphic Systems," J. Digit. Imag., 7(1), 13-17 (Feb. 1994).
Gilespy, T., et al, "Images on Personal Computers, Displaying Radiologic images on Personal Computers," J. Digit. Imag., 6(3), 151-163 (Aug. 1993).
Gilespy, T., et al, "Images on Personal Computers, Displaying Radiologic Images on Personal Computers: Practical Applications and Uses," J. Digit. Imag., 7(3), 101-106 (Aug. 1994).
Gilespy, T., et al, "Images on Personal Computers, Radiological images on Personal Computers: Introduction and Fundamental Principles of Digital Images," J. Digit. Imag., 6(2), 81-87 (May 1993).
Gillespie, G, "Image is Everything," Health Data Manag., (Nov. 1, 1999).
Gillespy, T., "About Dr Razz," ver. 0.95b8, (Oct. 30, 1998).
Grandinetti, L, et al, "CAMD and TeleEEG: Software Tools for Telemedicine Applications," In proceeding of: High-Performance Computing and Networking, International Conference and Exhibition, HPCN Europe 1998, Amsterdam, The Netherlands, Springer Berlin Heidelberg, 64-73 (Apr. 21-23, 1998).
Grevera, George J, dicom2pgm.c (1995).
Grevera, GJ, "A WWW to DICOM interface," Proc. SPIE, 2711, 109-117 (1996).
Halle, M, "Medical Visualization and Surgical Planning Using Open GL," Surgical Planning Laboratory, Brigham and Women's Hospital, 1998.
Harvy, D.J., "Software interface to allow querying and retrieval of DICOM images on a standard Web browser," Radiology 1997, Programme & Abstracts, 112 (May 19-21, 1997).
*Heart Imaging Technologies, LLC* v. *Merge Healthcare Incorporated*, Case No. 1:12-cv-1020, "Defendant Merge Healthcare, Inc.'S Second Supplemental Preliminary Invalidity Contentions," Aug. 23, 2013.
Henri, C., et al, "Design and Implementation of World Wide Web-Based Tools for Image Management in Computed Tomography, Magnetic Resonance Imaging, and Ultrasonogray," vol. 10, No. 3, Suppl. 1, 77-79 (Aug. 1997).
Hornof, W.J., et al, "Development of an Automated 12-8 Bit Conversion Algorithm for Displaying and Archiving Scanned Radiographs," Vet. Radiol. Ultrasound, 40(2), 179-182 (1999).
Kane, KC, et al (eds.), "A web access script language to support clinical application development," Computer Methods and Programs in Biomedicine, 55(2), 85-97 (1998).
Kim, Y, et al, "Handbook of Medical Imaging," vol. 3. Display and PACS, SPIE Press, Bellingham, WA (2000).
Komo, D, et al, "Multimedia medical data archive and retrieval server on the internet," Proc. SPIE, 3035, 72-75 (1997).
Koncar, M, et al, "WWW-based Image Management System," MIE 2000, IOS Press (2000).
Laird, SP, et al, Design and implementation of an Internet-based medical image viewing system, J. Systems and Software, 66, 167-181 (2003).
LEAD Technologies Introduces LEADTOOLS Medical Express Suite (Sep. 17, 1999).
Lehmann, TM, et al, "Content-based image retrieval in medical applications for picture archiving and communication systems," Proc. SPIE, 5033, 109-117 (2003).
Live Picture Launches Flagship Enterprise Image, PRNewswire, Live Picture, Inc. (Jul. 13, 1998).
Noro, R, et al, "Real-Time Telediagnosis of Radiological Images through an Asynchronous Transfer Mode network: The ArteMeD Project," J. Digital Imaging, 10(3), 116-121 (Aug. 1997).
Noro, R, et al, "Remote Inspection of Medical Images through High-speed Networks," EPFL, Lausanne, Switzerland (Jul. 1997).
Oberson, J-C, et al, "Development of an Electronic Radiologist's Office in a Private Institute," RadioGraphics, 20, 573-580 (2000).
Orphanoudakis, SC, et al, "I2C: A system for the indexing, storage, and retrieval of medical images by content," Med Inform (Lond)., 19(2), 109-122 (1994).
Ratib, O, et al, "Self contained off-line media for exchanging medical images using DICOM-compliant standard," Proc SPIE, 3980, 30-34 (2000).
Rubin, R, et al, "Web-Based Access to Teaching in a Filmless Radiology Environment," SPIE Conference on PACS Design and Evaluation: Engineering and Clinical Issues, vol. 3339, 520-528 (Feb. 1998).
Sakusabe, T, et al, "On-demand Server-side Image Processing for Web-based DICOM Image Display," Proc. SPIE, 3976, 359-367 (2000).

(56) References Cited

OTHER PUBLICATIONS

Smith, SE, "Exploring the Web for Medical Images," Information Today, 14(7), 14, 16 (Jul./Aug. 1997).

Stewart, B., et al, "DICOM Image Integration into an Electronic Medical Record Using Thin Viewing Clients," SPIE Conference on PACS Design and Evaluation: Engineering and Clinical Issues, vol. 3339, 322-328 (Feb. 1998).

Stewart, B., et al, "Integration of Multiple DICOM Webservers into an Enterprise-Wide Web-Based Electronic Medical Record," SPIE Conference on PACS Design and Evaluation: Engineering and Clinical Issues, vol. 3662, 52-59 (Feb. 1999).

Valenza, "Thin Wins," Imaging Economics, Mar. 2009, Retrieved from Internet on May 20, 2011 <URL: http://www.imagingeconomics.com/issues/articles/2009-03_02.asp>.

Vassallo, DJ, "Telemedicine kept simple," Images Paediatr. Cardiol., 2(2), 1-16 (Apr.-Jun. 2000).

Wingfield, N, "Server enhances databases' links to Web," InfoWorld (Jul. 19, 1995).

Wong, STC, et al, "A Digital Library for Biomedical Imaging on the Internet," IEEE Communication Magazine, 3(1), 84-91 (Jan. 1999).

\* cited by examiner

REMOTE CINE VIEWING OF MEDICAL IMAGES ON A ZERO-CLIENT APPLICATION

RELATED APPLICATIONS

This application is a continuation of patent application Ser. No. 13/305,442, filed Nov. 28, 2011, the entire contents of which are hereby incorporated by reference.

FIELD OF THE INVENTION

The present invention relates to remote cine viewing of medical images.

SUMMARY

In some embodiments, the invention provides a method of viewing medical images on a remote device using a zero-client web application. The method includes receiving, from a user, an image series selection via the zero-client web application and establishing a connection between the zero-client web application and a web server. The web application further receives series details from the web server and generates an off-screen image array according to the series data. Based on the series details, a buffering module outputs image requests to the web server, which is in communication with a medical image database storing images in a non-web browser compatible format. The zero-client web application receives, from the web server, converted medical images in response to the image requests. The converted medical images are in a web browser compatible format. The buffering module populates the off-screen image array with the converted medical images received from the web server. A display module sets a first converted medical image within the off-screen image array as an on-screen image to display the first converted medical image. Thereafter, the display module sets a next converted medical image from the off-screen image array as the on-screen image to display the next converted medical image in place of the first converted medical image. The display module then sequentially sets subsequent converted medical images of the off-screen image array as the on-screen image to stream the converted medical images.

In some embodiments, the invention provides a client device for remotely viewing medical images. The client device includes a zero-client web application, a communication interface, a buffering module, a memory, and a display module. The communication interface enables communications between the zero-client web application and a web server. The zero-client web application receives, from a user, an image series selection and receives, from the web server, series details corresponding to the image series selection. The zero-client web application further generates an off-screen image array according to the series details. The buffering module outputs image requests based on the image series selection to the web server, which is in communication with a medical image database storing images in a non-web browser compatible format. The memory stores the off-screen image array generated by the zero-client web application. The buffering module populates the off-screen image array with the converted medical images received from the web server in response to the image requests. The converted medical images are in a web browser compatible format. The display module sets a first converted medical image within the off-screen image array as an on-screen image to display the first converted medical image. Thereafter, the display module sets a next converted medical image from the off-screen image array as the on-screen image to display the next converted medical image in place of the first converted medical image. The display module then sequentially sets subsequent converted medical images of the off-screen array as the on-screen image to stream the converted medical images.

In some embodiments, the invention provides a computer readable medium including computer executable instructions that, when executed by a processor of a client device, generate a zero-client web application that enables remote viewing of medical images. The zero-client web application receives, from a user, an image series selection via the zero-client web application and establishes a connection between the zero-client web application and a web server. The zero-client web application further receives series details from the web server and generates an off-screen image array according to the series details. The zero-client web application includes a buffering module that outputs, based on the series details, image requests to the web server, which is in communication with a medical image database storing images in a non-web browser compatible format. The zero-client web application receives from the web server, converted medical images in response to the image requests. The converted medical images are in a web browser compatible format. The buffering module populates the off-screen image array with the converted medical images received from the web server. The zero-client web application also sets a first converted medical image within the off-screen image array as an on-screen image to display the first converted medical image, sets a next converted medical image from the off-screen image array as the on-screen image to display the next converted medical image in place of the first converted medical image; and sequentially sets subsequent converted medical images of the off-screen image array as the on-screen image to stream the converted medical images.

Other aspects of the invention will become apparent by consideration of the detailed description and accompanying drawings.

DETAILED DESCRIPTION

Figure 1:
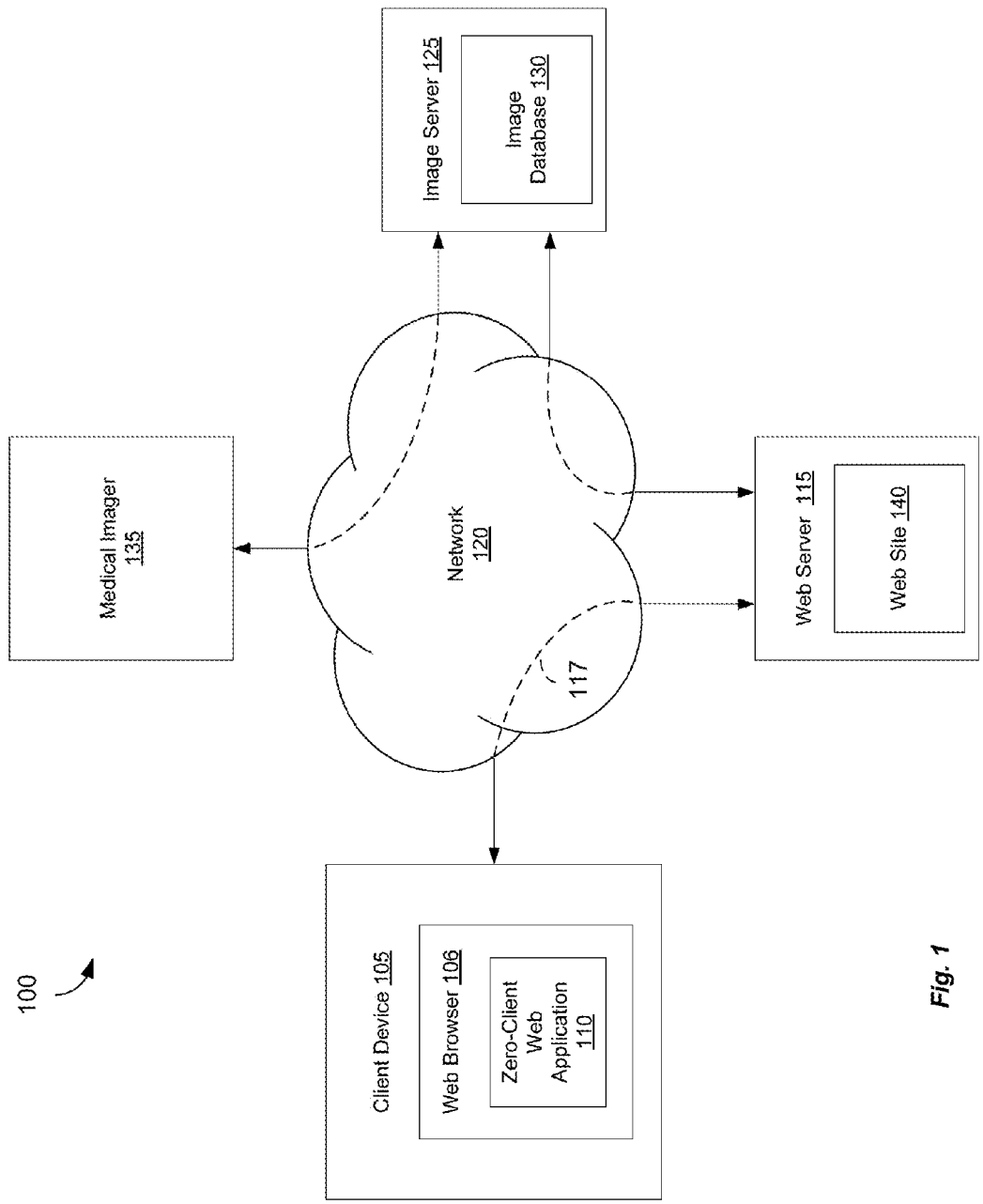
FIG. 1 depicts a system for remote viewing of medical images using a zero-client web application.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Additionally, although steps of methods are described herein as being executed in a particular order, in some instances, these steps may be executed in another order, simultaneously, and/or partially simultaneously.

In a client-server architecture, various functions are carried out by the client, and other functions are carried out by the server. The more functions performed by the client, rather than the server, the "thicker" the client. In contrast, the more functions performed by the server, rather than the client, the "thinner" the client. Accordingly, a thick client web application is an application executed by a web browser of a client device that typically provides extensive functionality independent of a central server. Thick client web applications consume computer resources and use operating system capabilities of the client device's operating system and installed libraries beyond the capabilities of a standard web browser. A thick client web application can, for instance, receive data (e.g., images) in a raw or intermediate state and process the data locally on the client device with less reliance on processing at the server. A thick client may also be referred to as a fat client, a heavy client, and a rich client. In contrast, a thin client web application executing on a client device relies on the processing power of the server. Thus, a thin client web application uses fewer computer resources and operating system capabilities of the client device than a thick client web application and typically uses a browser plugin or addon. A thin client web application uses, for instance, ActiveX, Flash, or Silverlight plugins where the plugin must exist on the client device or be installed before the web application can be used.

A zero-client web application is a web application that does not use web browser plug-ins or add-ons to extend the functionality of the core web browser program. Embodiments of the invention allow for remote cine viewing of medical images on a client device with a zero-client web application. In the context of this application, a zero-client web application means a web application executing in a standard web browser without browser plug-ins or add-ons for performing the remote image viewing functions described herein. In other words, a user of the client device does not need to install specialized plug-ins or add-ons to carry out the remote image viewing described in this application. The core web browser has sufficient processing capabilities to display and stream medical images that are compatible, such as Portable Network Graphics (PNG) or Joint Photographic Experts Group (JPEG) images, and the server performs the remaining image processing functions to render medical images in a format appropriate for the zero-client web application for display or streaming without plug-ins or add-ons. A zero-client web application is, for instance, HyperText Markup Language (HTML) and JavaScript code stored on a web server and downloaded and executed by a web browser.

FIG. 1 depicts a system 100 including a client device 105 with a web browser 106 that is executing a zero-client web application 110. The zero-client web application 110 is in communication with a web server 115 via a connection 117 over a network 120. The network 120 is one or more of the Internet, a local area network (LAN), a wide area network (WAN), and other computer networks. The client device 105 and web server 115 are coupled to the network 120 directly or indirectly by way of, e.g., a hub, router, or similar device. Such couplings include wired connections (universal serial bus (USB), Ethernet, etc.), wireless connections (e.g., Bluetooth, WiFi, cellular, etc.) or a combination thereof. The zero-client web application 110 may be stored on the web server 115 and a copy is transmitted to the web browser 106 in response to the user navigating the web browser 106 to a web site 140 generated by the web server 115. Thereafter, the web browser 106 executes the zero-client web application 110, as described in greater detail below.

The web server 115 is further in communication with an image server 125 via the network 120. The image server 125 stores medical images in an image database 130 generated by the medical imager 135. The medical imager 135 is one of a radiology imager, magnetic resonance imaging (MRI), computer tomography (CT) scan device, ultrasound device, thermo-graphic imaging device, or another imaging device that generates a medical image in a digital form. The image server 125 is in communication with the medical imager 135 via the network 120, either directly or via one or more intermediate systems that may be used in the communication of medical images. The images within the image database 130 include computed tomography (CT scan) images, magnetic resonance imaging (MRI) images, x-ray images, and other graphical depictions of patient medical information.

Although shown as connected through the network 120, in some instances, one or more of the client device 105, web server 115, image server 125, and medical imager 135 are directly coupled (e.g., via a wired connection or direct wireless connection) or coupled via independent networks. For instance, the client device 105 may be coupled to the web server 115 via the Internet, while the web server 115 and image server 125 are coupled via an independent local area network (LAN), and the image server 125 and medical imager 135 are directly coupled.

The client device 105 is one of a personal computer, kiosk, tablet, laptop, mobile phone device (e.g., an iPhone®, Blackberry®, Droid®, etc.), or other computing device with an ability to connect to the network 120 and run the browser 106 to execute the zero-client web application 110. The client device 105 includes a processor that executes the browser 106, zero-client web application 110, and other software stored in a memory associated with the client device 105. In some embodiments, one or more of the software programs are stored remotely from the client device 105. The zero-client web application 110 may be stored on a computer readable medium, such as a hard disk, compact disc, flash drive, or other non-transitory, tangible computer readable medium. Additionally, although the zero-client web application 110 is described herein as software executed by a processor of the client device 105, in some instances, the zero-client web application 110 and other software are implemented partially or completely in hardware (e.g., using a field programmable gate array (FPGA) or application specific integrated circuit (ASIC)).

The client device 105 further includes a power source, a display (e.g., a touch screen display), user inputs (e.g., push buttons, scroll wheels, a keyboard, a mouse, a microphone), user outputs (e.g. speakers), and a network communications interface for interfacing with the network 120. The power source is, for instance, a battery that provides power to the components of the client device 105. In some instances, the power source receives power from an external battery, wall outlet, or other external power source, and provides the power to components of the client device 105.

The zero-client web application 110 provides a graphical user interface (GUI) on the display of the client device 105. The GUI enables the user to interact with the zero-client web application 110 by way of the display, user input, audio in/out, etc.

Figure 2:
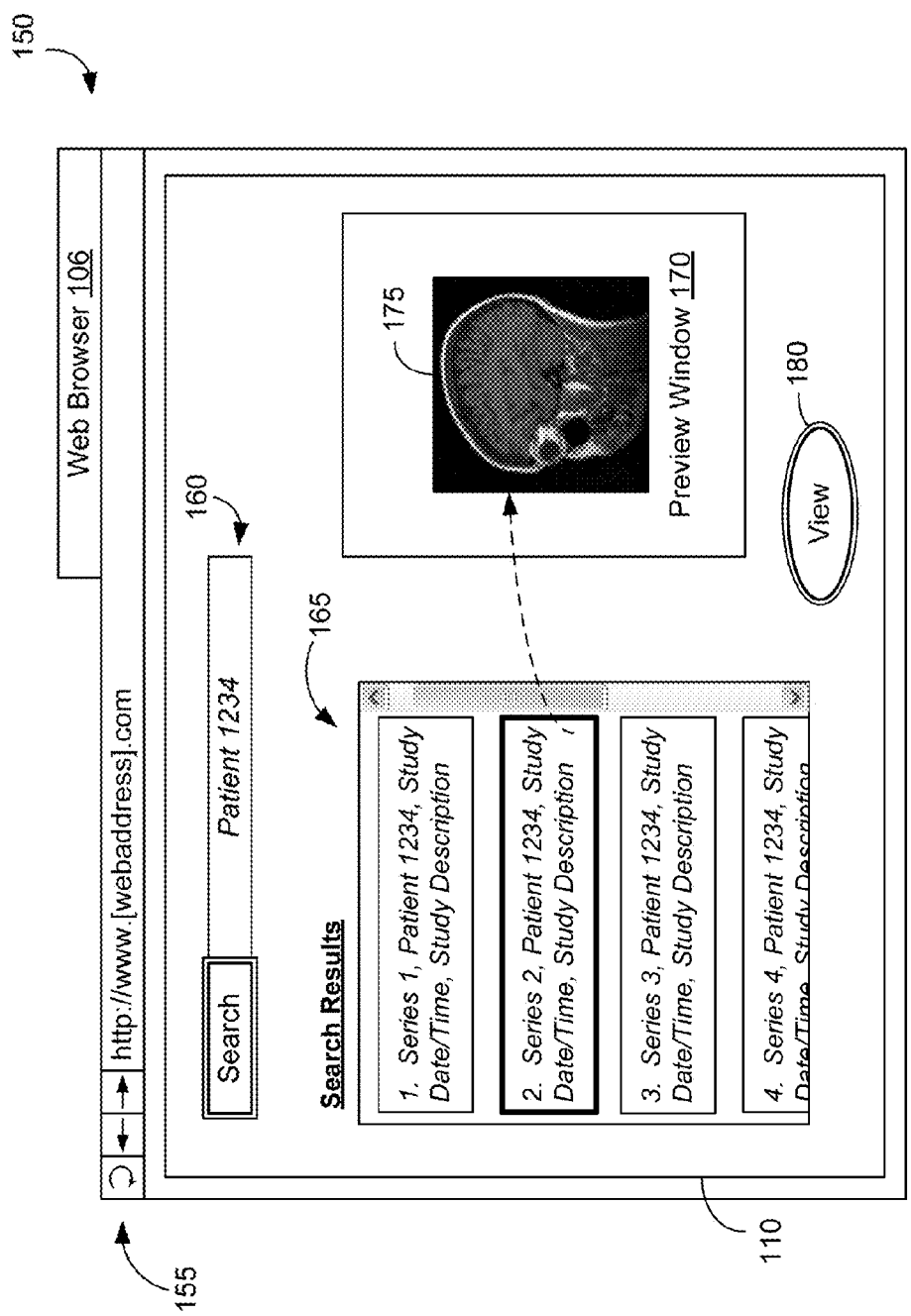
FIGS. 2-3 depict a graphical user interface of a zero-client web application.

FIG. 2 illustrates an exemplary GUI 150 of the zero-client web application 110. The GUI 150 is generated by the zero-client web application 110 in response to receiving data from the web site 140. The GUI 150 includes navigation tools 155, a search tool 160, a series list 165, and a preview window 170. The search tool 160 enables a user to enter keywords, patient identifiers, and other search parameters to locate and identify images in the image database 130. Medical images within the image database 130 may be grouped together to form an image series. For example, a CT scan may result in a sequence of images that form an image series.

The series list 165 includes a list of image series including series 1, series 2, series 3, and series 4, each of which includes one or more medical images associated with an example patient identifier "patient 1234." The series list 165 may include the series most recently viewed by the user, the results of a search performed using the search tool 160, or other series. A thumbnail 175 representative of a highlighted series within series list 165 is shown in the preview window 170. A user can highlight a series by hovering a mouse over the series, clicking on the series with a mouse, or selecting the series via a touch screen display, among other I/O techniques.

Figure 3:
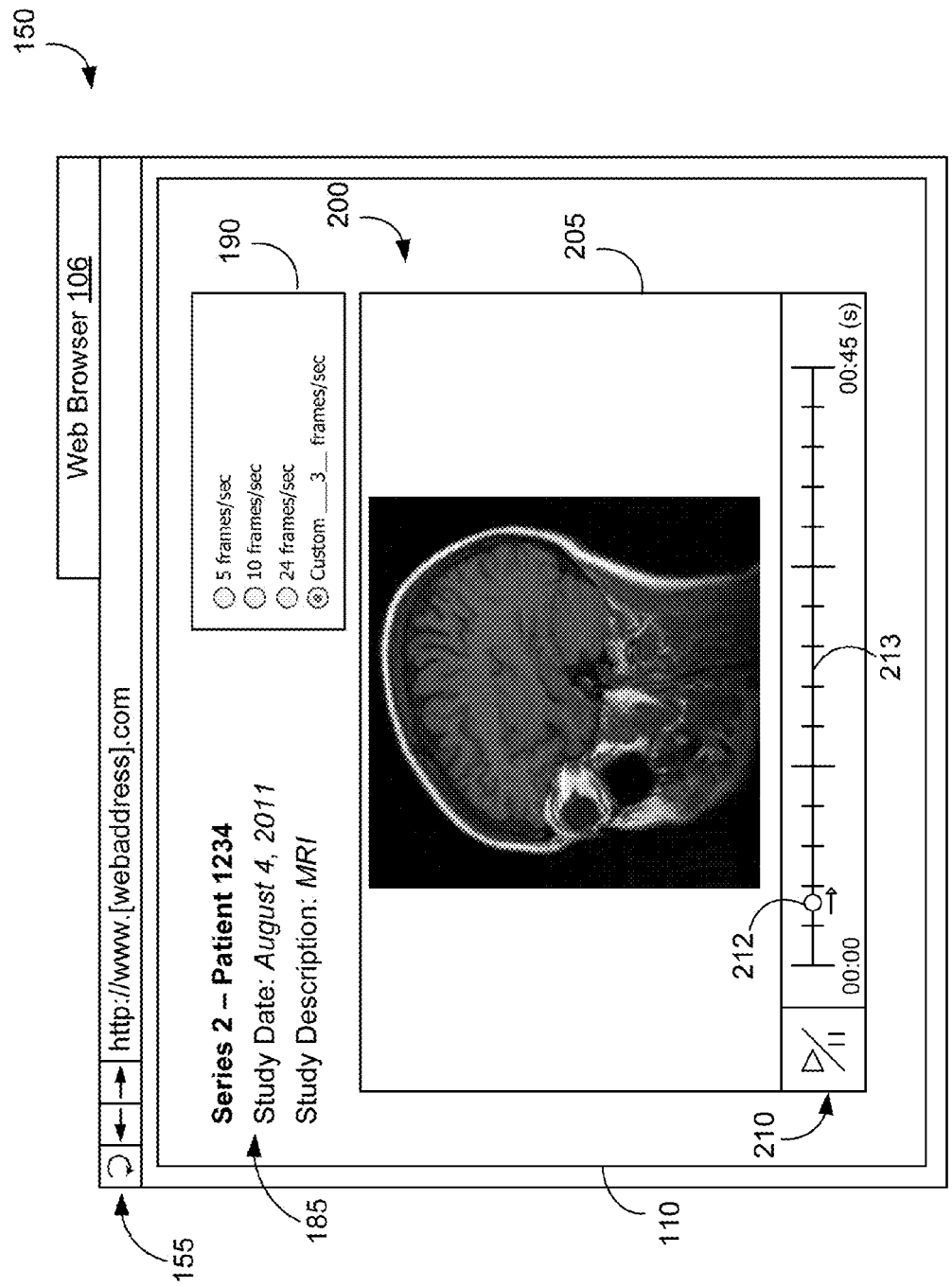

By selecting the view button 180, double clicking on a series within series list 165, or using another I/O technique, the GUI 150 is updated as shown in FIG. 3. The GUI 150 of FIG. 3 includes series information 185, a frame rate selector 190, and a series player 200 including a display window 205 and player controls 210. The series information 185 lists details of the series selected as described above with respect to FIG. 2. The series information 185 includes a patient identifier (i.e., patient 1234), which may be the patient's name, patient identification number, or another unique identifier. The series information 185 may also include the date that the study was created (e.g., the date of a CT scan), a description of the study (e.g., neural MRI scan, kidney ultrasound, etc.), additional patient information (e.g., age, previous diagnoses), previous notes made by medical staff regarding the patient or the series, and other information.

The user interacts with the player controls 210 to start, pause, skip, and restart the playing of a series of images in the display window 205. A slider 212 along timeline 213 indicates the elapsed time of the image series playback. The user may also drag the slider 212 to adjust the image being displayed in the display 205. The frame rate selector 190 enables a user to specify the playback frame rate for the series in the series player 200. The user may specify one of a set of predetermined frame rate options, or specify a particular frame rate. In some embodiments, a frame rate slider is included in the frame rate selector 190 that enables a user to specify a frame rate by sliding a scroll left and right or up and down to increase/decrease the frame rate. Other user I/O techniques are also contemplated for specifying the frame rate, including touch screen actions and voice commands. As will be described in further detail below, the images of a series are sequentially sent by the web server 115 to the client device 105. When the series player 200 begins to play a series, a portion of the images of a series may still be in transit from the web server 115. The images of the series that have been received, however, may be streamed by the series player 200 as the additional images continue to be received.

FIGS. 4A-F illustrate a process 300 for remote viewing of medical images according to embodiments of the invention. Initially, a user requests an image series via the GUI 150 of the zero-client web application 110, for example, by selecting an image series as described in FIG. 2 to proceed to the screen illustrated in FIG. 3. The GUI 150 generates an image series request 305 and provides the image series request 305 to an initial request module 310. The initial request module 310 generates a hypertext transfer protocol (HTTP) request 315 including a Uniform Resource Locator (URL) with dynamically generated query parameters that describe the image series requested. The initial request module 310 then transmits the HTTP request 315 to an HTTP request handler 325 of the web server 115.

The HTTP request handler 325 translates the HTTP request 315 to a series load request 330 for an image rendering module 335. The HTTP request handler 325 also generates a Digital Imaging and Communications in Medicine (DICOM) request 340 based on the series load request 330. The DICOM request 340 is sent to the image database 130, which includes medical images in a DICOM format or another format generally incompatible with web browsers lacking particular add-ons or plug-ins.

Figure 4A:
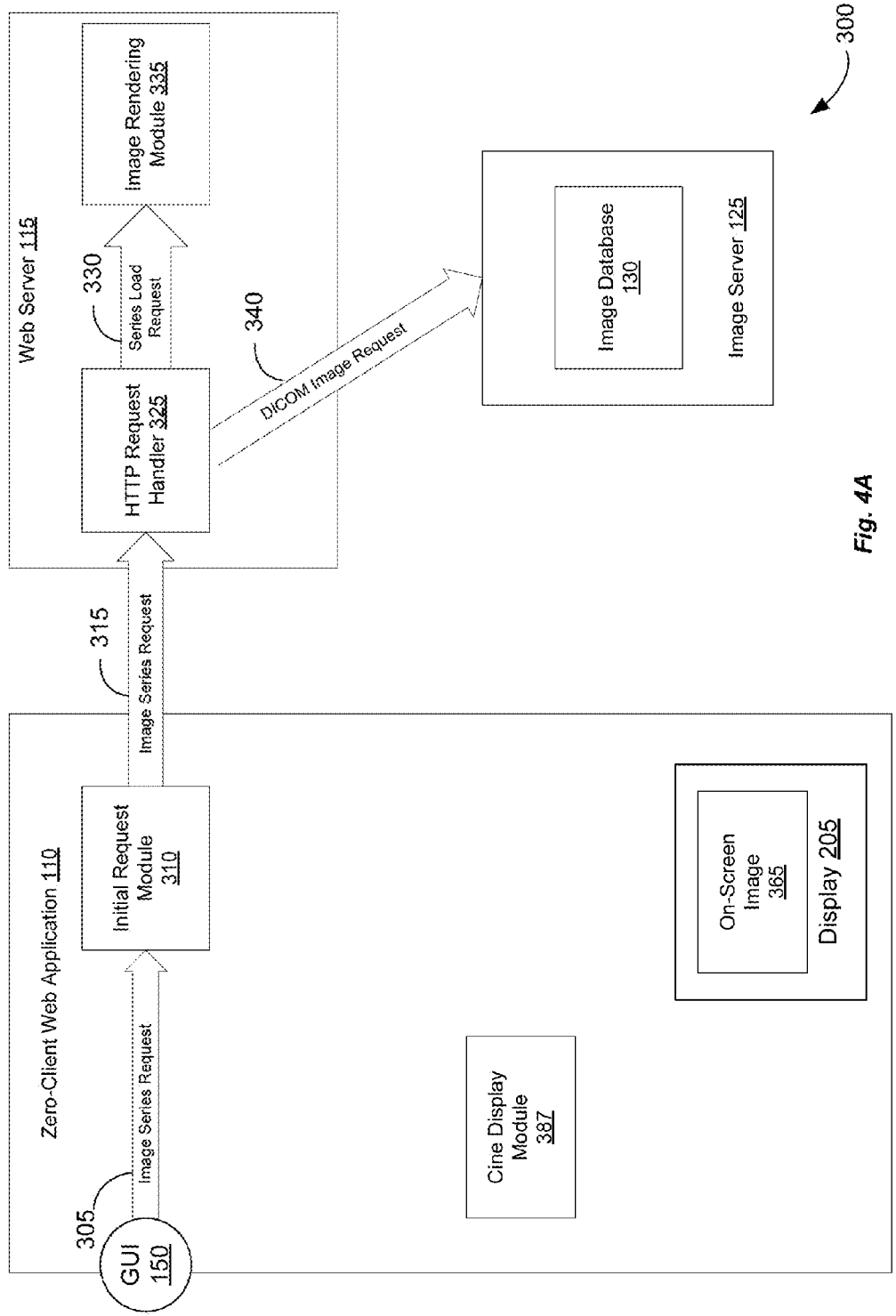
FIGS. 4A-F depict a process for remote cine viewing of medical images according to embodiments of the invention.
Figure 4B:
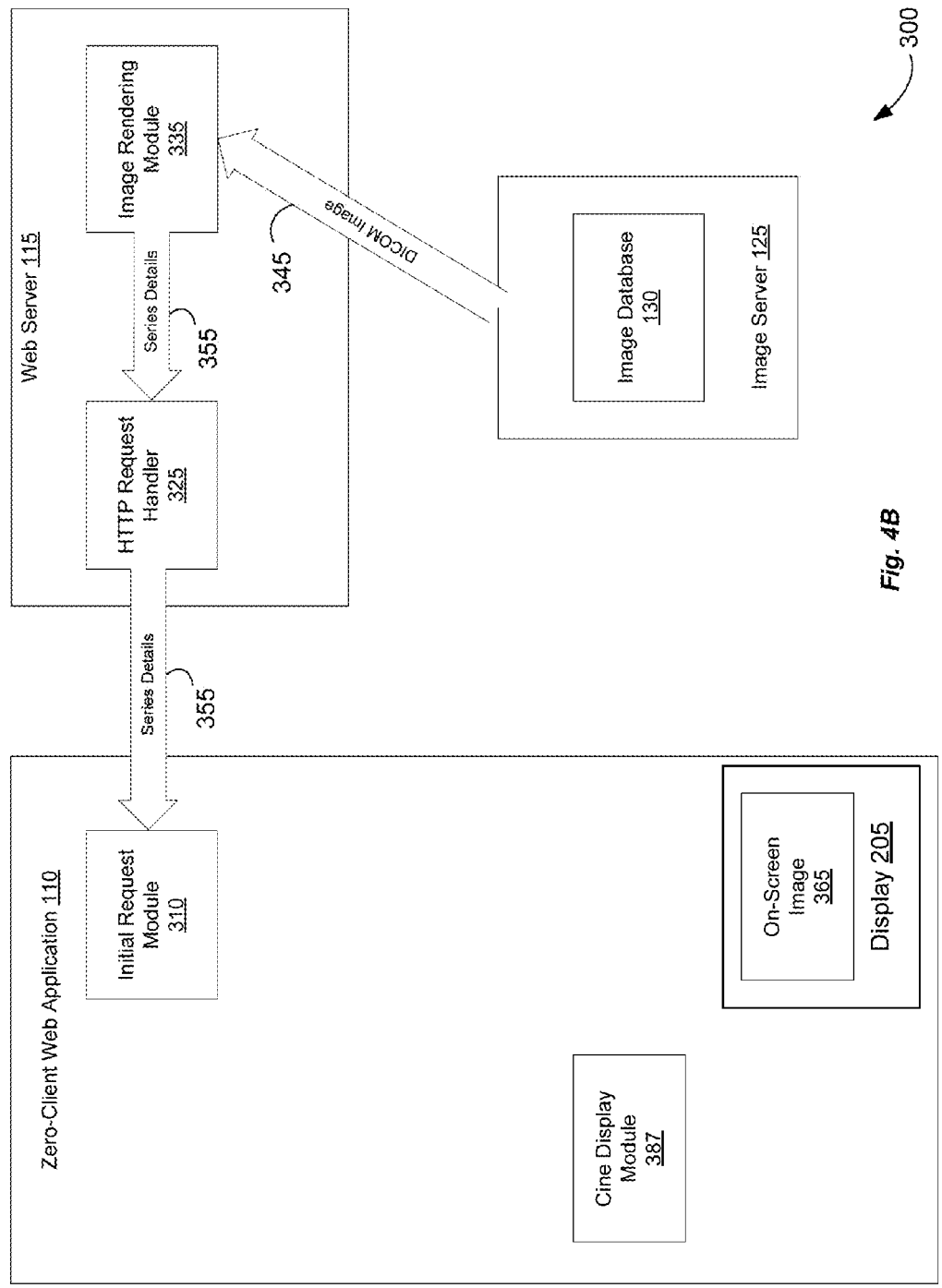

Turning to FIG. 4B, the image database 130 returns DICOM image 345, to the image rendering module 335 in response to the DICOM request 340. The image rendering module 335 receives additional information for the requested image series (series details 355). The series details 355 indicates the number of frames associated with the series specified in the image series request 305 and includes image frame information used by the zero-client web application 110 to dynamically generate a URL for each frame. Each URL may point to a single-frame DICOM image or may point to a single frame within a multi-frame DICOM image.

The HTTP request handler 325 forwards the series details 355 to the initial request module 310. Upon receipt, the initial request module 310 stores the series details 355 in a memory (not shown) of the client device 105.

Figure 4C:
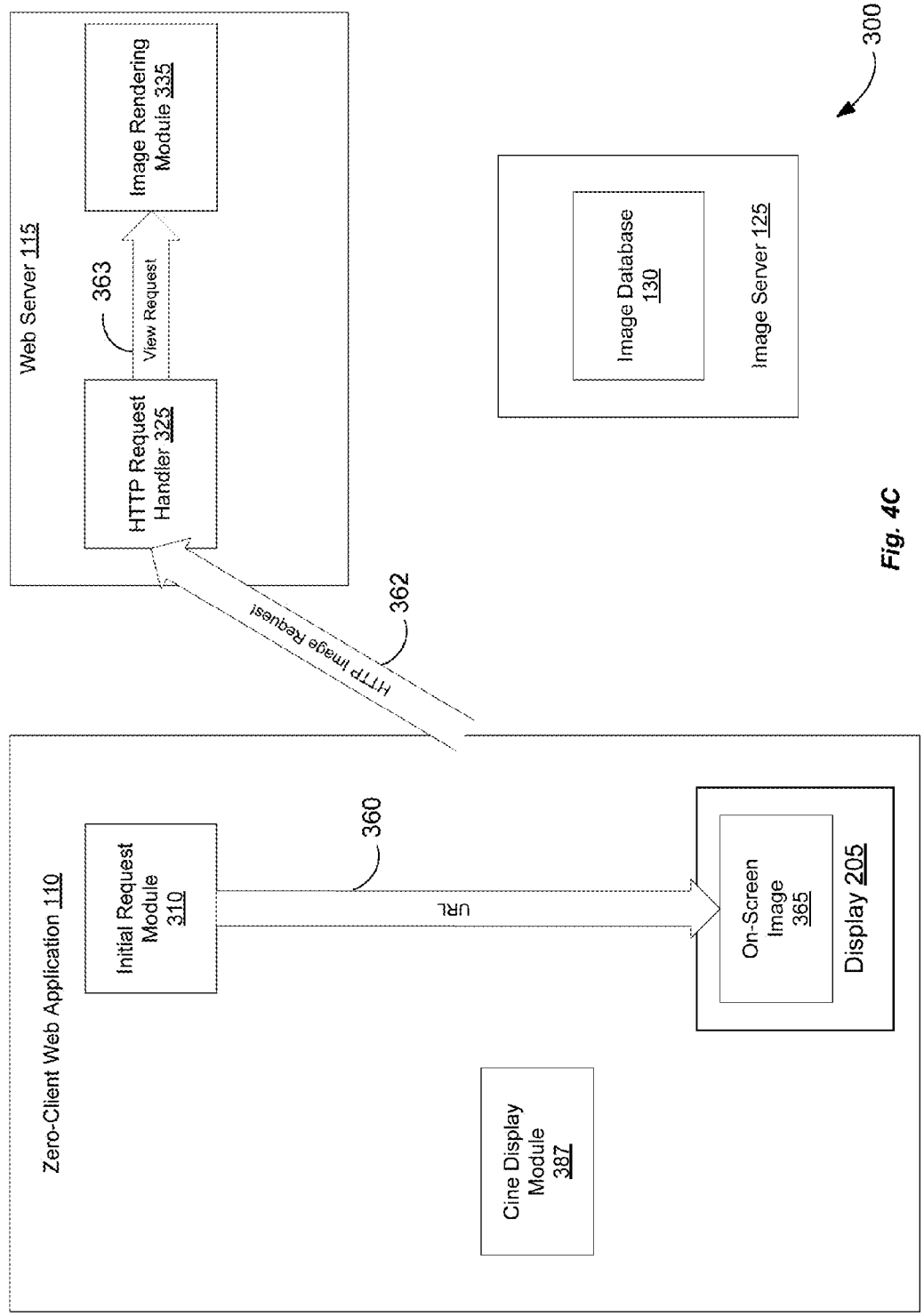

Turning to FIG. 4C, the initial request module 310 detects the current display settings of the display window 205. The display settings include the size of the display window 205 (e.g., 1200×1400 pixels). The initial request module 310 generates a Uniform Resource Locator (URL) 360 with dynamically generated query parameters that specify the first image of the requested image series and describe the image view requested. Further, the zero-client web application 110 sets the "src" attribute of an on-screen image 365 to the URL 360 to cause the zero-client web application 110 to generate an HTTP image request 362 to request the first image of the requested image series. The zero-client web application 110 then transmits the HTTP request 362 to an HTTP request handler 325 of the web server 115.

The HTTP request handler 325 translates the HTTP request 362 to a view request 363 for an image rendering module 335. The HTTP request handler 325 recognizes that the first DICOM image 345 was received by the web server 115 in response to the earlier DICOM image request 340 and does not re-send the request to the image server 125.

Figure 4D:
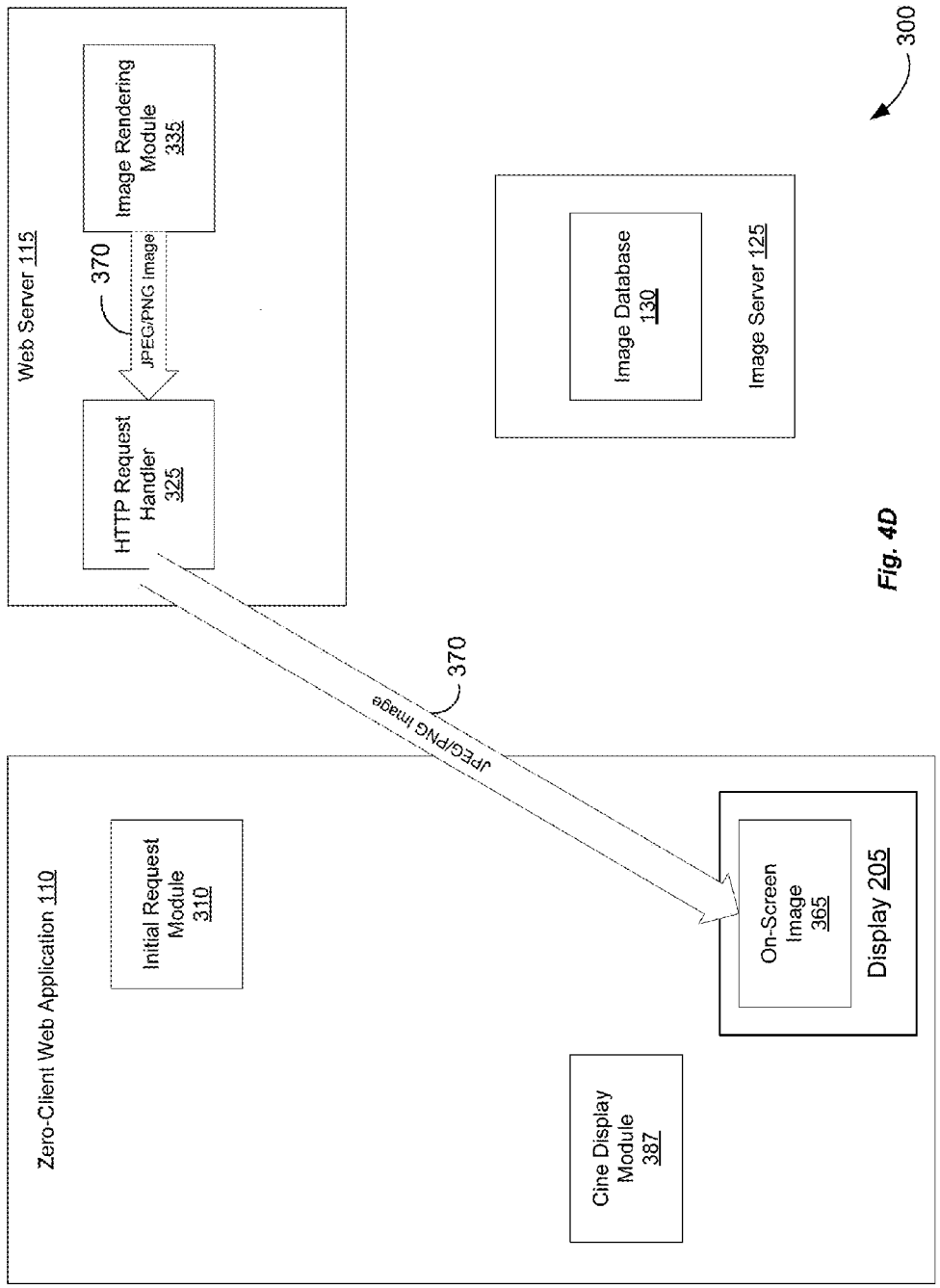

As shown in FIG. 4D, the image rendering module 335 converts the DICOM image 345 into a web browser compatible image 370. The web browser compatible image 370 is generated according to the display settings of the view request 363. For instance, the web browser compatible image 370 is sized according to the display settings. The web browser compatible image 370 is, for instance, a JPEG or PNG formatted image, which is displayable by the zero-client web application 110 and browser 106 without specialized plug-ins or add-ons.

The HTTP request handler 325 forwards the web browser compatible image 370 to the zero-client web application 110. Upon receipt by the zero-client web application 110, the web browser compatible image 370 is set to the on-screen image 365 and is visible to the user in the display 205.

Figure 4E:
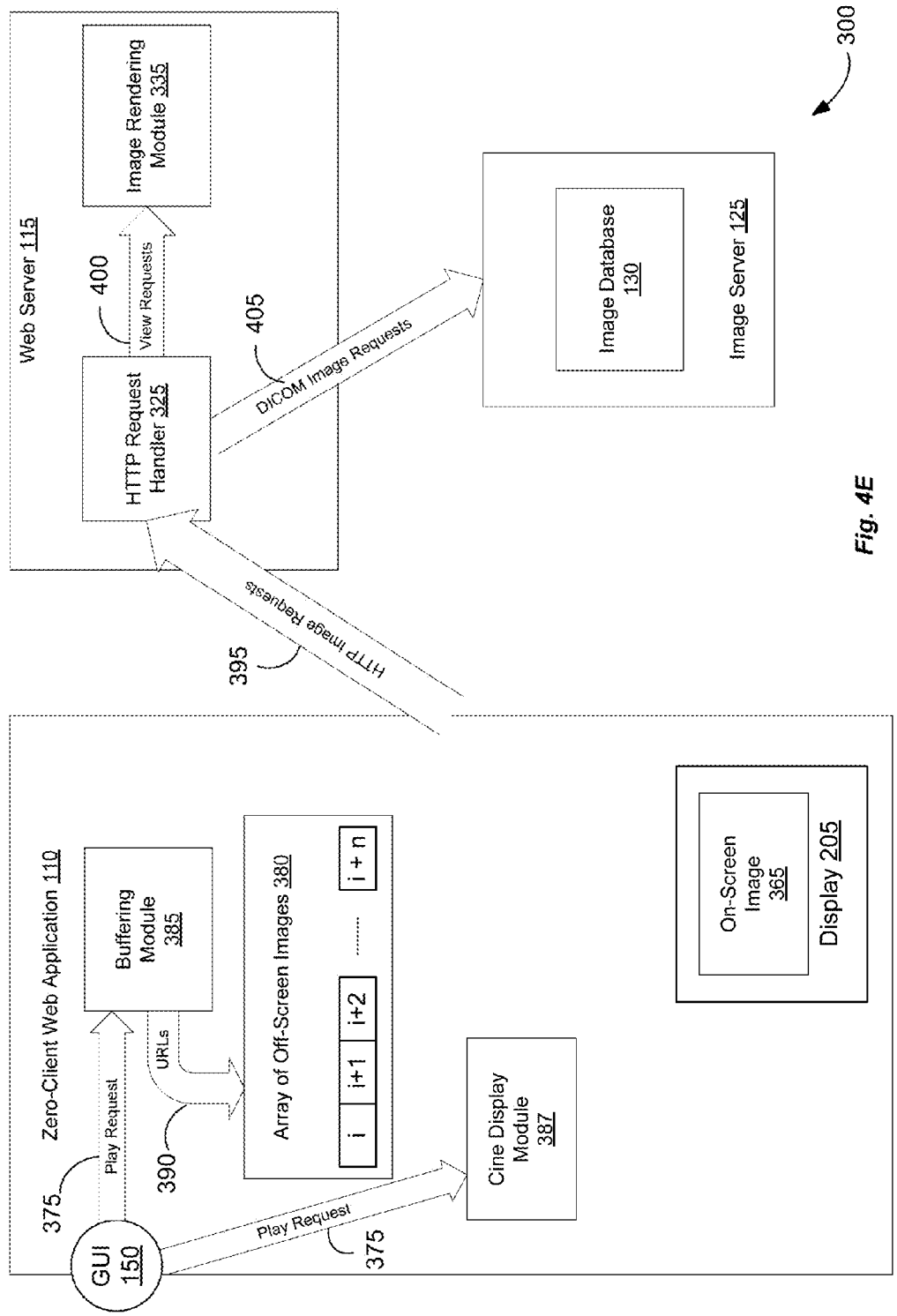

To begin a cine playback of the requested image series, the user selects the play button of player controls 210. Turning to FIG. 4E, the GUI 150 outputs a play request 375, including the series details 355, to a buffering module 385 and a cine display module 387. In some instances, the zero-client web application 110 automatically generates the play request 375 without user input via GUI 150 after the first frame of the requested series (web browser compatible image 370) is displayed via the on-screen image 365.

Once the play request 375 is received by the buffering module 385, the buffering module 385 generates an array of off-screen images 380, which may be stored in a memory (not shown) of the client device 105. The array of off-screen images 380 includes one element for each frame of the requested image series, as indicated by the series details 355. Each element of the array of off-screen images 380 includes a "src" attribute that is initially set to an empty value. Additionally, in contrast to the on-screen image 365, each element of the array of off-screen images 380 is not visible to a user of the zero-client web application 110.

After creation of the array of off-screen images 380, the buffering module 385 begins setting the "src" attribute of each element of the array of off-screen images 380 to a URL 390 representing an image frame view. Setting each "src" attribute to one of the URLs 390 causes the zero-client web application 110 to generate HTTP requests 395 to request each image frame of the requested image series. The zero-client web application 110 then transmits each HTTP image request 395 to the HTTP request handler 325 of the web server 125. The buffering module 385 will set the "src" attributes in a controlled manner such that a limited number of requests are outstanding at any given time.

The HTTP request handler 325 translates each HTTP request 395 to a view request 400 for the image rendering module 335. The HTTP request handler 325 also generates a DICOM request 405 based on the URL for each HTTP image request 395 and sends each DICOM request 405 to the image database 130.

Figure 4F:
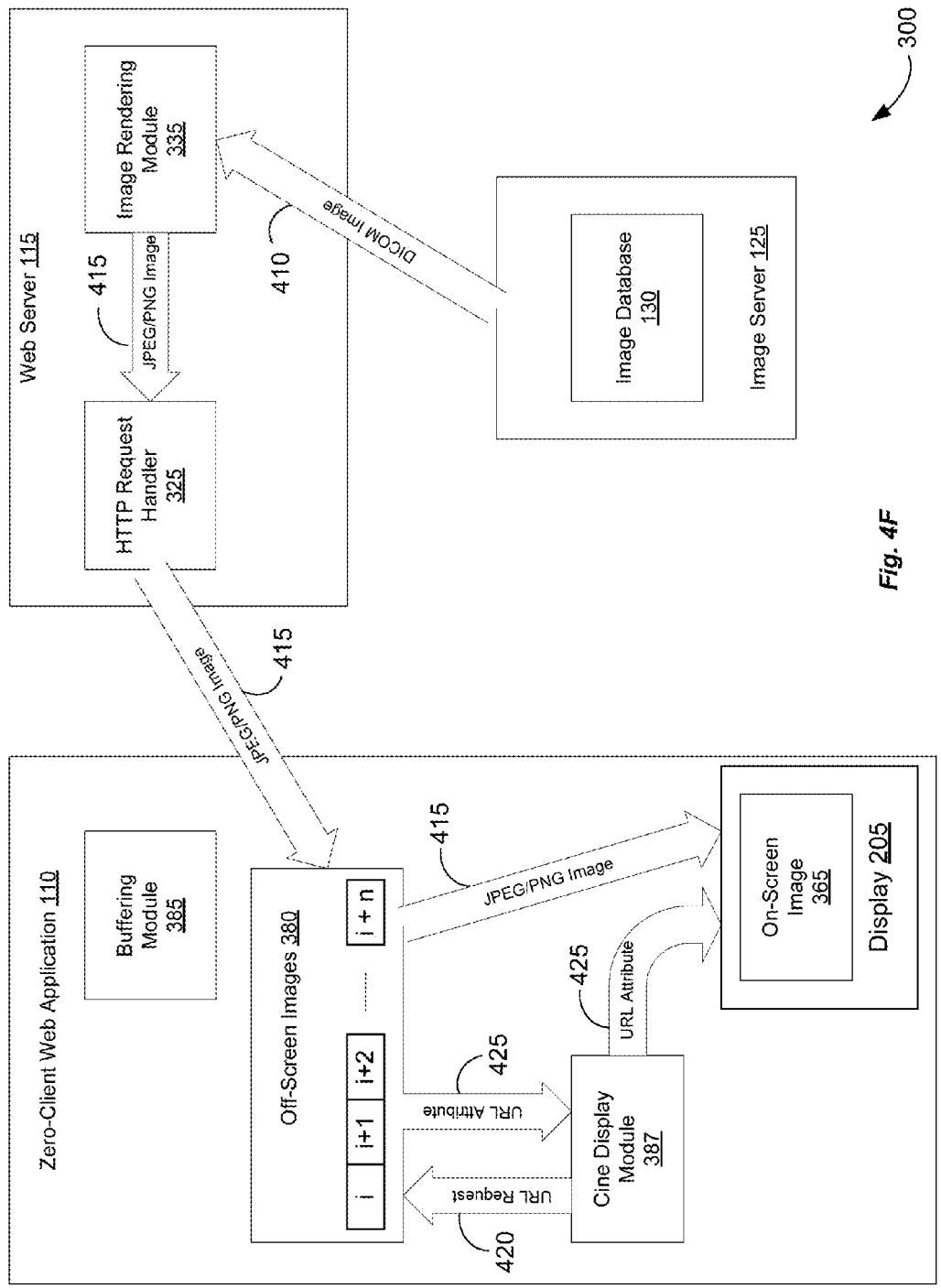

Turning to FIG. 4F, the image database 130 returns a DICOM image 410 (or a frame thereof for multi-frame DICOM images) for each DICOM request 405 to the image rendering module 335. The image rendering module 335 converts each DICOM image 410 into a web browser compatible image 415. Each web browser compatible image 415 is generated according to the display settings of its corresponding view request 400. The web browser compatible images 415 are, for instance, JPEG or PNG formatted images, which are displayable by the zero-client web application 110 and browser 106 without specialized plug-ins or add-ons.

The HTTP request handler 325 forwards the web browser compatible images 415 to the zero-client web application 110, which sequentially stores each web browser compatible image 415 in the array off-screen images 380, one web browser compatible image 415 per element of the array of off-screen images 380.

Although the images 415 are described as being stored in the array of off-screen images 380, the images may be stored in a local client memory and the web browser 106 or web application 110 construes the URLs within the elements of the array of off-screen images 380 as pointing to their respective images 415 in the local client memory. Additionally, the locally stored web browser compatible images 415 may be generally inaccessible to a user via a folder structure of an operating system GUI. That is, a user cannot navigate through an operating system GUI to a folder storing temporary Internet/web browser files to locate the web browser compatible images 415. By preventing such access to users, the retrieved medical images are secured and the zero-client web application 110 complies with certain government regulations related to patient privacy. In some instances, the array of off-screen images 380 is deleted upon closing of the browser 106, navigating away from the web site 140 using the web browser 106, or after a predetermined amount of time of user inactivity at the web browser 106. Accordingly, another user without authorization to view the medical images is not able to later retrieve and view them.

As the web browser compatible images 415 are received by the zero-client web application 110, the cine display module 387 begins streaming the web browser compatible images 415. To stream the web browser compatible images 415, the cine display module 387 sends a URL request 420 to the array of off-screen images 380 to request the "src" attribute of the second element (i+1) of the array of off-screen images 380. The array of off-screen images 380 returns a URL address 425 for the second element of the array. The cine display module 387 replaces the "src" attribute of the on-screen image 365 with the retrieved URL 425. Accordingly, the on-screen image 365 will point to a location of memory storing the web browser compatible image 415 associated with the second element (i+1) of array 380, which is then retrieved and displayed by the zero-client web application 110 in the display 205. The "src" attribute of the on-screen image 365 is then updated with the "src" attribute of the remaining elements of the array of off-screen images 380 (i.e., elements i+2, i+3, etc.), one-by-one in sequence, to stream the web browser compatible images 415.

Figure 5:
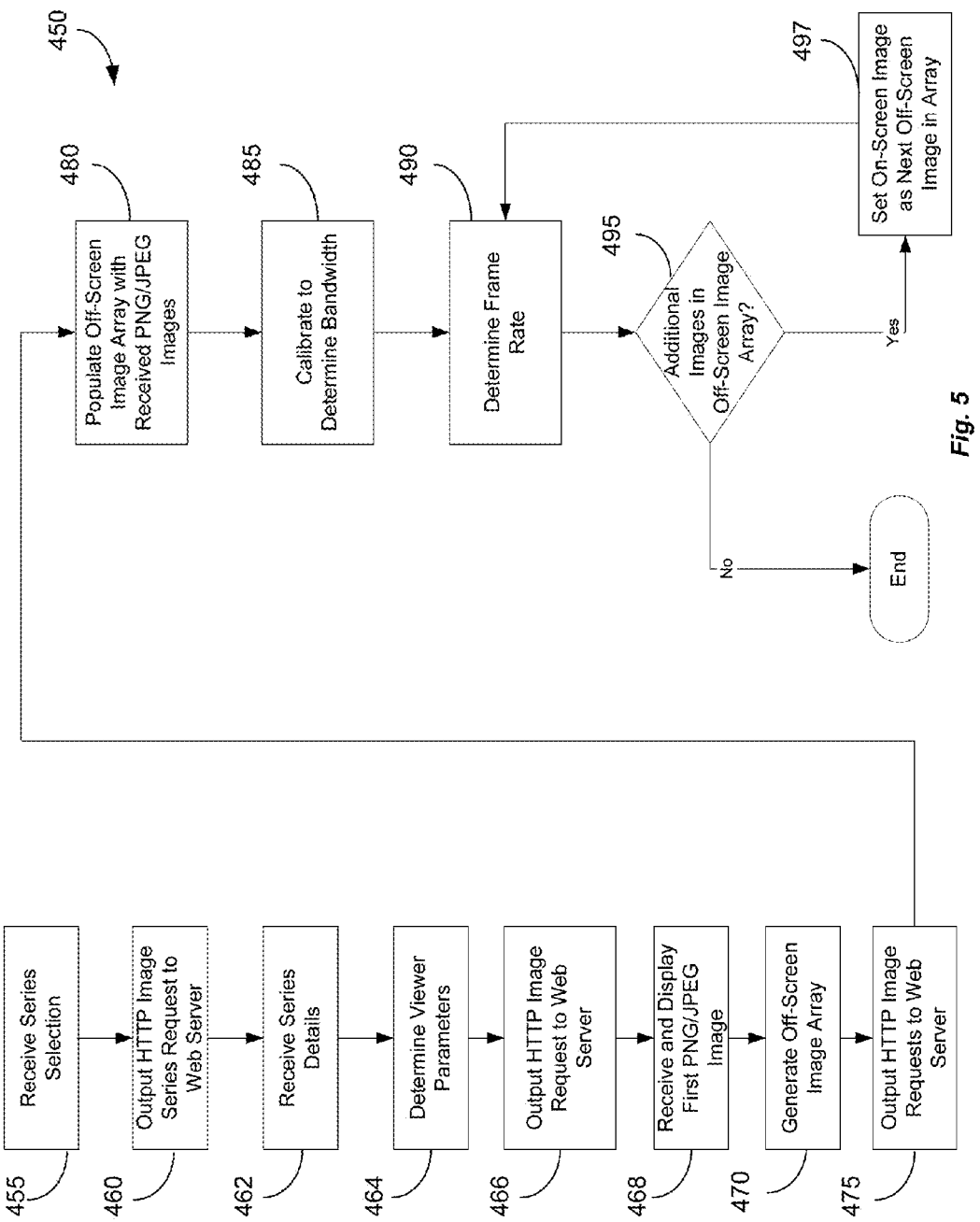
FIG. 5 depicts a method of streaming remotely stored images on a zero-client web application according to embodiments of the invention.

FIG. 5 illustrates a method 450 of streaming remotely stored images on a zero-client web application according to embodiments of the invention. In step 455, the zero-client web application 110 receives a user request for an image series via the GUI 150. In step 460, the zero-client web application 110 outputs an HTTP series request 315 to the web server 115. In step 462, the zero-client web application 110 receives the series details 355. In step 464, the initial request module 310 determines the viewer parameters for the display window 205, such as the window size, image quality, and the user-selected frame rate for playback. In step 466, the zero-client web application 110 outputs an HTTP image request 362 to the web server 115. In step 468 the zero-client web application 110 receives the web browser compatible image 370, which is displayed in the display window 205.

In step 470, the zero-client web application 110 creates the array of off-screen images 380 according to the series details 355. In step 475, the zero-client web application 110 generates and outputs the HTTP image requests 395 to web server 115. In step 480, the zero-client web application 110 populates the array of off-screen images 380 with web browser compatible images 415 received from the web server 115. The zero-client web application 110 continues to populate the array of off-screen images 380 until the transfer of web browser compatible images 415 is completed; however, the zero-client web application 110 simultaneously proceeds through the remaining steps of method 450.

In step 485, the zero-client web application 110 performs a calibration step to determine a sustainable frame rate based on the average bandwidth detected for the connection 117 between the application 110 and the web server 115. The sustainable frame rate is the rate at which a series of images may be streamed from the web server 115 to the display window 205 of the zero-client web application 110 without stalling to wait for receipt of further images. For instance, if the zero-client web application 110 is receiving images at a frame rate of ten frames/second from the web server 115, the application 110 can play back the images at a frame rate of ten images/second or less without stalling. In one embodiment, the zero-client web application 110 determines the amount of time elapsed to download a first predetermined amount of web browser compatible images 415 (i.e., frames) to determine the sustainable frame rate. For instance, if the first ten images take two seconds to download, the sustainable frame rate is five frames/second.

Figure 6:
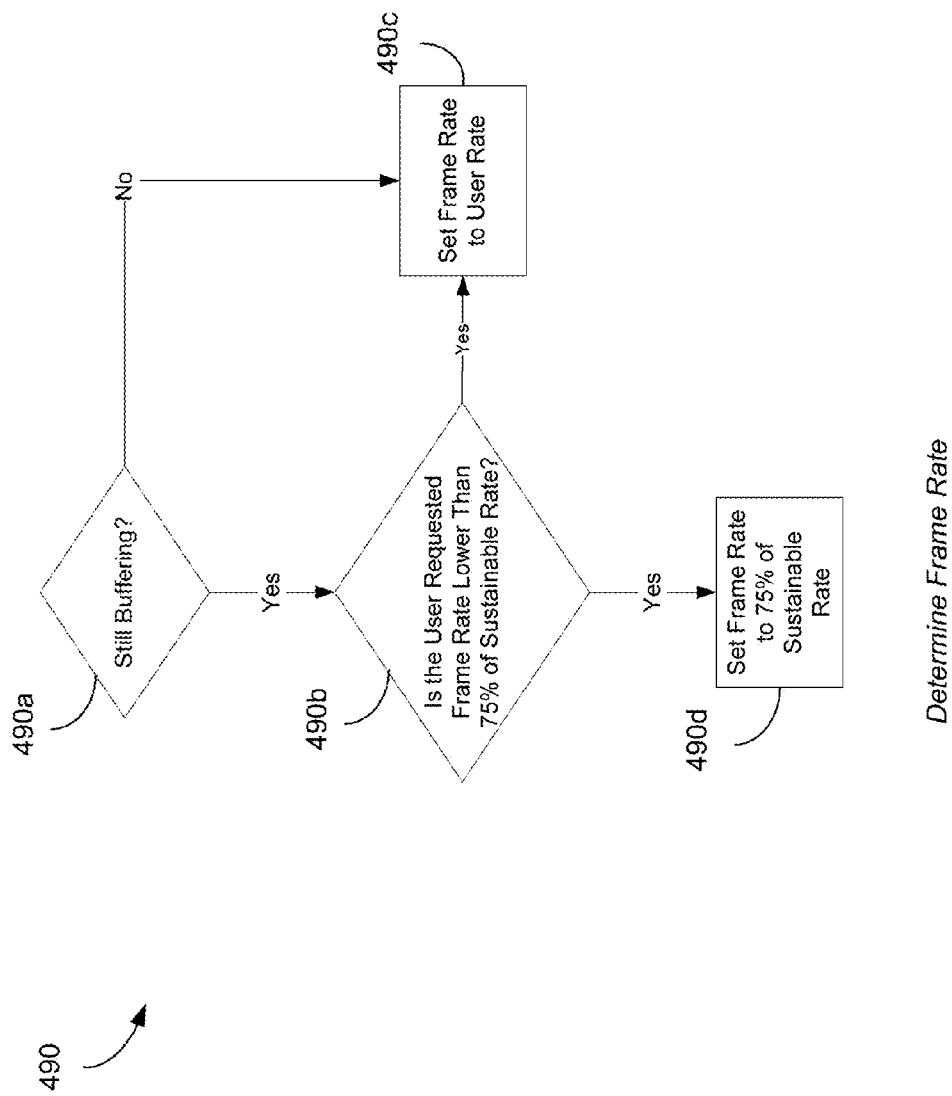
FIG. 6 depicts a method for determining a frame playback rate.

In step 490, the zero-client web application 110 determines the frame rate for playback. Step 490 is illustrated in greater detail in FIG. 6. In step 490a, the cine display module 387 determines whether the buffering module 385 is still receiving web browser compatible images 415 from the web server 115 for playback on the display 205 (i.e., whether the buffering module 385 is still buffering). If the buffering module 385 is still buffering, as will likely be the situation as the first image is about to be displayed, the cine display module 387 proceeds to step 490b. In step 490b, the cine display module determines whether the user-selected frame rate is less than 75% of the sustainable frame rate determined by calibration in step 470. If the user-selected frame rate is less than 75% of the sustainable frame rate, the cine display module 387 sets the playback frame rate to the user-selected frame rate (step 490c). If, however, the user-selected frame rate is greater than or equal to 75% of the sustainable frame rate, the cine display module 387 sets the playback frame rate to 75% of the sustainable frame rate (step 490d). By selecting the lower of the two frame rates, the cine display module 387 improves the likelihood that the playback of the requested image series will not be stalled in the display 205. If buffering is complete, as determined in step 490a, all of the requested web browser compatible images 415 are stored locally in the array of off-screen images 380. Accordingly, the cine display module 387 sets the playback frame rate to the user selected frame rate, as the risk of stalling due to the bandwidth of connection 117 no longer exists. Although 75% of the sustainable rate is used as a threshold in step 490b and a playback rate in 490d of FIG. 6, in some instances, other thresholds and playback rates are used (e.g., 50%, 90%, or 100%).

Returning to FIG. 5, in step 495, the cine display module 387 determines whether additional images are within the array of off-screen images 380. If additional images are present, in step 495, the cine display module 387 obtains the "src" attribute of the next image within the array of off-screen images 380. Continuing in step 497, the cine display module 387 sets the "src" attribute of the on-screen image 365 to the "src" attribute of the next image, causing the next image to be displayed in the display window 205. Step 497 is executed at a time that is appropriate to reach the desired frame rate as determined in step 490. For instance, to achieve 25 frames/ second, step 497 is executed ⅟25 seconds after the previous setting of the "src" attribute of the on-screen image 365. Steps 490, 495, and 497 are repeated until the last image of the web browser compatible images 415 within the array of off-screen images 380 is displayed in display window 205. After the last image is displayed, the cine display module 387 may continue to display images at the requested frame rate starting again at the first image (i.e., a loop playback). In some instances, the zero-client web application 110 may perform a yo-yo playback, where the images are displayed from image 1 to n, then shown in reverse order from image n to 1. In some instances, the zero-client web application 110 may stop playback upon reaching the last image of a requested image series.

In some embodiments, the user may specify the amount of memory that may be used by the zero-client web application 110 to store web browser compatible images 370 and 415. For instance, the user may specify the memory space available to the zero-client web application 110 using the GUI 150, similar to the technique for the user to specify a frame rate using the frame rate selector 190. Alternatively, the user may specify the memory space available using a preferences window/screen of the GUI (not shown). If a requested image series requires more memory space than specified by the user, the zero-client web application 110 may skip image frames in the playback of the requested image series (for example, it may only request and display every third frame) or may use a rolling window in memory. In the rolling window implementation, when the memory available to the zero-client web application 110 has been filled, the zero-client web application 110 overwrites previously received web browser compatible images 370 and 415 with subsequently received web browser compatible images 415. For example, if memory capacity is filled when storing a PNG image associated with element (i+50) of the array of off-screen image 380, the zero-client web application 110 stores the next PNG image for element (i+51) at the location in memory where the PNG image for element (i) is stored. In other words, the (i+51) image overwrites the (i) image. Thereafter, the (i+52) image will overwrite the (i+1) image, the (i+53) image will overwrite the (i+2) image, and so forth. In this example, no more than fifty-one PNG images occupy the local memory at one time.

Figure 7:
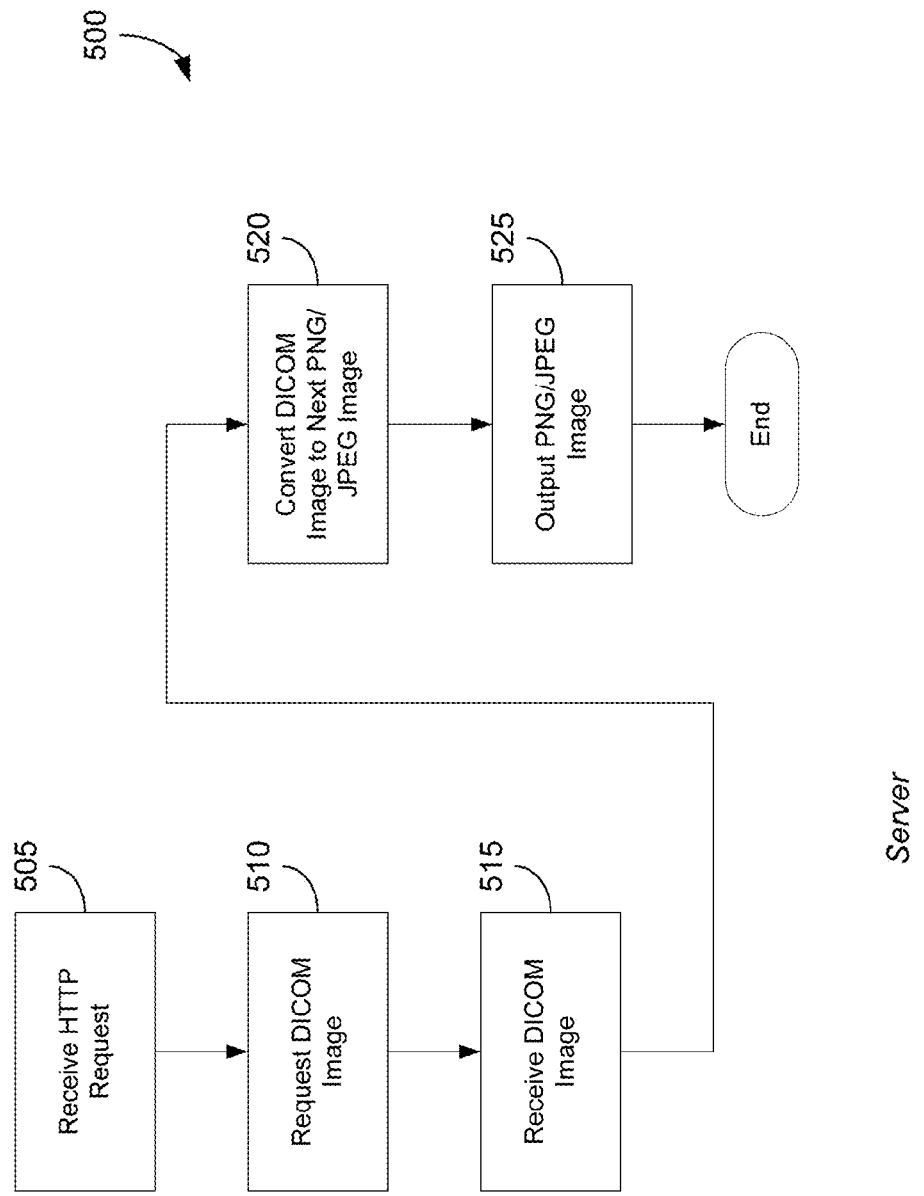
FIG. 7 depicts a method for handling a request from a zero-client web application for medical images stored in an incompatible format.

FIG. 7 illustrates a method 500 for the web server 115 to handle a request from a zero-client web application 110 for medical images stored in an incompatible format. In step 505, the HTTP request handler 325 of the server 115 receives the HTTP request 362 or 395 for an image from the zero-client web application 110. In step 510, the HTTP request handler 325 generates a DICOM image request 340 or 405. The DICOM image request 340 or 405 is sent to the image server 125. The image database 130 of the image server 125 receives the DICOM image request 340 or 405 and provides the requested DICOM image 345 or 410 to the web server 115. In step 515, the DICOM image 345 or 410 is received by the image rendering module 335 of the web server 115. In step 520, the image rendering module 335 converts the DICOM image 345 or 410 into the web browser compatible image 370 or 415. In step 525, the image rendering module 335 outputs the web browser compatible image 370 or 415 to the HTTP request handler 325, which outputs the web browser compatible image 370 or 415 to the zero-client web application 110.

Although the zero-client web application 110 has been described as providing the ability to remotely view medical images, the zero-client web application 110 includes additional functionality in some embodiments. For example, a user may annotate medical images shown on the display 205, zoom in/out on the medical images shown on the display 205, associate text (e.g., a user description, comment, and/or medical opinion) with the medical image series or medical images shown on the display 205, and/or send or forward (e.g., via email) to other entities the medical image series or medical images shown on the display 205. Additional operations a user can implement via the zero-client web application 110 include: adjust contrast, adjust brightness, zoom in/out, pan, rotate, grey-scale inversion, display of cross-reference lines, mirror, textual annotations, various line and angle measurement annotations, print, share with other users, and transfer to other storage devices.

Additionally, although the system 100 is described as for use with remotely viewing DICOM images stored in image database 130, other the system 100 may also be used for retrieving other file types. For instance, the system 100 may further be used for remote viewing of JPEG, PNG, TIFF, and BMP images. Additionally, the system 100 may also be used for remote viewing of DICOM structured reports and clinical document architecture (CDA) documents.

Thus, embodiments of the invention provide, among other things, systems and methods for remote cine viewing of medical images on a zero-client web application.

What is claimed is:
1. A method of viewing medical images on a remote device using a zero-client web application, the method comprising:

receiving an image series selection via the zero-client web application, the zero-client web application in communication with a web server;

outputting image requests to the web server based on the image series selection, wherein the web server is in communication with a medical image database storing images in a non-web browser compatible format;

receiving, from the web server, converted medical images in response to the image requests, wherein the converted medical images are in a web browser compatible format;

populating an off-screen image array with the converted medical images received from the web server; and streaming the converted medical images on the zero-client web application using the off-screen image array.

2. The method of claim 1, further comprising:
receiving series details from the web server; and
generating, by the zero-client web application, the off-screen image array according to the series details.

3. The method of claim 1, further comprising:
determining a bandwidth of a connection between the zero-client web application and the web server;
determining a sustainable streaming rate based on the bandwidth;
receiving, from the user, a requested streaming rate via the zero-client web application; and
during a buffering stage, streaming the medical images at a frame rate that is the lower of the requested streaming rate and a percentage of the sustainable streaming rate.

4. The method of claim 3, further comprising:
determining that the web server has completed sending the medical images in response to the image series request; and
streaming the medical images at the requested streaming rate.

5. The method of claim 1, wherein streaming the converted medical images comprises:
setting a first medical image within the off-screen image array as an on-screen image to display the first medical image;
setting a next medical image from the off-screen image array as the on-screen image to display the next medical image in place of the first medical image; and
sequentially setting subsequent medical images of the off-screen image array as the on-screen image to stream the medical images.

6. The method of claim 5, wherein setting the next medical image from the off-screen image array as the on-screen image includes setting a src attribute of the on-screen image to a src attribute of the next medical image.

7. The method of claim 1, further comprising:
obtaining viewer parameters including a window size that indicates a size of a display window of the zero-client web application; and
outputting the viewer parameters to the web server,
wherein the received medical images have been formatted by the web server according to the viewing parameters.

8. The method of claim 1, wherein the web browser compatible format is one of Portable Network Graphics (PNG) and Joint Photographic Experts Group (JPEG) and the non-web browser compatible format is Digital Imaging and Communications in Medicine (DICOM).

9. A client device for remotely viewing medical images, the client device comprising:
a communication interface enabling communications between a zero-client web application and a web server, wherein the zero-client web application receives an image series selection;

a buffering module that outputs image series requests to the web server, wherein the web server is in communication with a medical image database storing images in a non-web browser compatible format;

an off-screen image array populated with converted medical images received from the web server in response to the image series requests, wherein the converted medical images have been converted to a web browser compatible format from the images in the medical image database in the non-web browser compatible format; and a display module that streams the converted medical images on the zero-client web application using the off-screen image array.

10. The client device of claim 9, wherein the display module further
determines a bandwidth of the connection between the zero-client web application and the web server;
determines a sustainable streaming rate based on the bandwidth;
receives, from a user, a requested streaming rate via the zero-client web application; and
streams the converted medical images at a frame rate that is the lower of the requested streaming rate and a percentage of the sustainable streaming rate.

11. The client device of claim 10, wherein the display module further
determines that the web server has completed sending the converted medical images in response to the image series request, and
streams the converted medical images at the requested streaming rate.

12. The client device of claim 9, wherein streaming the converted medical images using the off-screen image array includes setting a src attribute of an on-screen image to a src attribute of a converted medical image.

13. The client device of claim 9, wherein
the zero-client web application determines viewer parameters including a window size that indicates a size of a display window of the zero-client web application,
the buffering module outputs the viewer parameters to the web server, and
the received converted medical images are formatted by the web server according to the viewing parameters.

14. The client device of claim 9, wherein
the zero-client web application further receives series details from the web server corresponding to the image series selection and generates the off-screen image array according to the series details; and
the buffering module populates the off-screen image array with the converted medical images received from the web server.

15. A method of viewing medical images on a remote device using a zero-client web application, the method comprising:
receiving an image series selection via the zero-client web application;
establishing a connection between the zero-client web application and a web server;
receiving series details from the web server;
generating, by the zero-client web application, an off-screen image array according to the series details;
outputting, by a buffering module, image requests to the web server based on the series details, wherein the web server is in communication with a medical image database;

receiving, from the web server, medical images in response to the image requests, the medical images being in a web browser compatible format;

populating, by the buffering module, the off-screen image array with the medical images received from the web server;

displaying a first medical image from the off-screen image array as an on-screen image to display the first medical image;

displaying a next medical image from the off-screen image array as the on-screen image in place of the first medical image; and sequentially displaying subsequent medical images of the off-screen image array as the on-screen image to stream the medical images.

16. The method of claim 15, further comprising:

determining a bandwidth of the connection between the zero-client web application and the web server;

determining a sustainable streaming rate based on the bandwidth;

receiving, from the user, a requested streaming rate via the zero-client web application; and during a buffering stage, streaming the medical images at a frame rate that is the lower of the requested streaming rate and a percentage of the sustainable streaming rate.

17. The method of claim 16, further comprising:

determining that the web server has completed sending the medical images in response to the image series request; and streaming the medical images at the requested streaming rate.

18. The method of claim 15, wherein displaying the next medical image from the off-screen image array as the on-screen image includes setting a src attribute of the on-screen image to a src attribute of the next medical image.

19. The method of claim 15, further comprising:

obtaining viewer parameters including a window size that indicates a size of a display window of the zero-client web application; and outputting, by the buffering module, the viewer parameters to the web server, wherein the received medical images are formatted by the web server according to the viewing parameters.

20. The method of claim 15, wherein the medical image database includes images stored in Digital Imaging and Communications in Medicine (DICOM) format.

* * * * *